US011555022B2

(12) United States Patent
Qian

(10) Patent No.: US 11,555,022 B2
(45) Date of Patent: Jan. 17, 2023

(54) POLYFUNCTIONAL OXETANE-BASED COMPOUND AND PRODUCTION METHOD THEREOF

(71) Applicants: CHANGZHOU TRONLY NEW ELECTRONIC MATERIALS CO., LTD., Changzhou (CN); CHANGZHOU TRONLY ADVANCED ELECTRONIC MATERIALS CO., LTD., Changzhou (CN)

(72) Inventor: Xiaochun Qian, Changzhou (CN)

(73) Assignees: CHANGZHOU TRONLY NEW ELECTRONIC MATERIALS CO., LTD., Changzhou (CN); CHANGZHOU TRONLY ADVANCED ELECTRONIC MATERIALS CO., LTD., Changzhou (CN)

( * ) Notice: Subject to any disclaimer, the term of this patent is extended or adjusted under 35 U.S.C. 154(b) by 222 days.

(21) Appl. No.: 17/089,931

(22) Filed: Nov. 5, 2020

(65) Prior Publication Data
US 2021/0053929 A1 Feb. 25, 2021

Related U.S. Application Data

(60) Division of application No. 16/246,113, filed on Jan. 11, 2019, now Pat. No. 10,906,882, which is a continuation of application No. PCT/CN2017/092227, filed on Jul. 7, 2017.

(30) Foreign Application Priority Data

Jul. 13, 2016 (CN) .......................... 201610548580.7

(51) Int. Cl.
C07D 305/06 (2006.01)
C08G 59/18 (2006.01)
C08G 65/18 (2006.01)
C07D 407/12 (2006.01)
C07D 407/14 (2006.01)
C08G 65/08 (2006.01)

(52) U.S. Cl.
CPC ......... C07D 305/06 (2013.01); C07D 407/12 (2013.01); C07D 407/14 (2013.01); C08G 59/18 (2013.01); C08G 65/18 (2013.01); C08G 65/08 (2013.01)

(58) Field of Classification Search
CPC .. C07D 305/06; C07D 407/12; C07D 407/14; C08G 59/18; C08G 65/18; C08G 65/08; C08G 59/12
USPC ......................................................... 549/510
See application file for complete search history.

(56) References Cited

U.S. PATENT DOCUMENTS

| | | | |
|---|---|---|---|
| 2,895,931 | A | 7/1959 | Klug |
| 3,111,470 | A | 11/1963 | Marans |
| 3,209,013 | A | 9/1965 | Hechenbleikner et al. |
| 3,341,475 | A | 9/1967 | Vandenberg |
| 4,946,992 | A | 8/1990 | Falk et al. |
| 5,663,289 | A | 9/1997 | Archibald et al. |
| 6,015,914 | A | 1/2000 | Sasaki et al. |
| 6,084,004 | A | 7/2000 | Weinmann et al. |
| 6,166,101 | A | 12/2000 | Takami |
| 6,284,898 | B1 | 9/2001 | Moszner et al. |
| 6,495,636 | B2 | 12/2002 | Sugiyama et al. |
| 6,586,496 | B1 | 7/2003 | Takamatsu et al. |
| 6,770,737 | B2 | 8/2004 | Kakushi et al. |
| 7,423,097 | B2 | 9/2008 | Inata |
| 7,524,610 | B2 | 4/2009 | Kim et al. |
| 7,534,820 | B2 | 5/2009 | Kohno et al. |
| 7,902,305 | B2 | 3/2011 | Kong |
| 8,883,942 | B2 | 11/2014 | Frank et al. |
| 9,249,126 | B2 | 2/2016 | Kim et al. |
| 9,575,409 | B2 | 2/2017 | Ng et al. |
| 9,822,088 | B2 | 11/2017 | Wohl et al. |
| 2003/0158286 | A1 | 8/2003 | Nishizaki et al. |
| 2005/0061429 | A1 | 3/2005 | Hosaka |
| 2005/0288386 | A1 | 12/2005 | Ishikawa |
| 2006/0025542 | A1 | 2/2006 | Musa |
| 2011/0052831 | A1 | 3/2011 | Kyota |
| 2011/0190418 | A1 | 8/2011 | Noguchi et al. |
| 2014/0093699 | A1 | 4/2014 | Xu |

(Continued)

FOREIGN PATENT DOCUMENTS

| | | |
|---|---|---|
| CN | 101155853 | 4/2008 |
| CN | 103497691 | 1/2014 |

(Continued)

OTHER PUBLICATIONS

International Search Report and Written Opinion dated Oct. 10, 2017 in connection with PCT patent application No. PCT/CN2017/092227.
Li et al., Polyurethane Resin, Mar. 31, 1992, pp. 6, 7, 40, and 41.
Second Office Action dated Aug. 20, 2020 in connection with Chinese App. No. 201610548580.7.

(Continued)

Primary Examiner — Taylor V Oh
(74) Attorney, Agent, or Firm — Pillsbury Winthrop Shaw Pittman, LLP

(57) ABSTRACT

A group of polyfunctional oxetane-based compounds having a structure as represented by general formula (I) or a product obtained by a reaction between a compound of general formula (I) and epichlorohydrin, an ester compound, or an isocyanate compound. When these polyfunctional oxetane-based compounds are used as cation polymerizable monomers in combination with an epoxy compound, the curing speed is high, and the cured product has highly excellent hardness, flexibility, adherence, and heat resistance.

10 Claims, No Drawings

(56) References Cited

U.S. PATENT DOCUMENTS

2016/0083505 A1  3/2016  Tanaka
2018/0237579 A1  8/2018  Fujikawa et al.

FOREIGN PATENT DOCUMENTS

| | | |
|---|---|---|
| CN | 104447635 | 3/2015 |
| CN | 106397660 | 4/2019 |
| EP | 2206745 | 7/2010 |
| JP | H06016804 | 1/1994 |
| JP | H114003264 | 5/1999 |
| JP | H11152441 | 6/1999 |
| JP | H11246541 | 9/1999 |
| JP | H132001002760 | 1/2001 |
| JP | H132001302651 | 10/2001 |
| JP | H132001302652 | 10/2001 |
| JP | H132001310937 | 11/2001 |
| JP | H142002128888 | 5/2002 |
| JP | H142002161134 | 6/2002 |
| JP | H152003193018 | 7/2003 |
| JP | H172005002191 | 1/2005 |
| JP | H172005255671 | 9/2005 |
| JP | H172005320491 | 11/2005 |
| JP | H202008535975 | 4/2008 |
| JP | H202008297271 | 12/2008 |
| JP | H212009079070 | 4/2009 |
| JP | H212009084523 | 4/2009 |
| JP | H212009256553 | 11/2009 |
| JP | H222010254893 | 11/2010 |
| JP | H232011168561 | 9/2011 |
| TW | 251123 | 3/2006 |
| WO | 2001022165 | 3/2001 |
| WO | 2009057737 | 3/2011 |
| WO | 2016066146 | 5/2016 |

OTHER PUBLICATIONS

Pragnacharyulu et al., "Adenosine Deaminase Inhibitors: Synthesis and Biological Evaluation of Unsaturated, Aromatic, and Oxo Derivatives of (+)-erythro-9-(2"S Hydroxy3"R-nonyl)adenine [(+)-EHNA]", J. Med. Chem. 43 (2000), pp. 4694-4700.

Office Action dated Oct. 31, 2019 in connection with Japanese App. No. 2018-565662.

Office Action dated Nov. 19, 2019 in connection with Chinese App. No. 201610548580.7.

Search Report dated Dec. 19, 2019 in connection with European App. No. 17826940.3.

Notice of Allowance issued in corresponding U.S. Appl. No. 16/246,113, dated Nov. 17, 2020.

POLYFUNCTIONAL OXETANE-BASED COMPOUND AND PRODUCTION METHOD THEREOF

This application is a divisional of U.S. patent application Ser. No. 16/246,113, filed Jan. 11, 2019, which is a continuation of PCT Patent Application No. PCT/CN2017/092227, filed Jul. 7, 2017, which claims the benefit of priority of Chinese Patent Application No. 201610548580.7, filed Jul. 13, 2016, each of the foregoing application is incorporated herein in its entirety by reference.

FIELD

This description involves organic chemistry, and particularly a polyfunctional oxetane-based compound and a production method thereof.

In the field of photocuring, the cationic photocuring system has advantages of being not affected by oxygen polymerization inhibition, having small shrinkage of cured volume, and the like. Active diluent monomers used therein mainly include vinyl ether-based compounds, epoxy-based compounds, and oxetane-based compounds.

SUMMARY

Cured products having good heat resistance, adhesion, and chemical resistance can be obtained from epoxy-based monomers, but reactivities of the monomers are relatively low. Vinyl ether-based monomers have high polymerization activity but have poor hardness, abrasion resistance, chemical resistance, and the like, and cannot be used as hard coating agents or protective films of various base materials. By comparison, oxetane-based monomers have high reactivity and their products, after curing, have excellent physical properties, and are being more widely used in curable compositions. In particular, the combined use of an oxetane-based monomer and an epoxy-based monomer (for combining advantages of both monomers) has become a common form of cationic photocuring systems.

In recent years, favorable improvements of application have been achieved by multi-functionalizing the oxetane-based monomers. For example, Chinese Patent Application Publication No. CN103497691A discloses a photocurable binder composition used in the production of a polarizer, wherein a bifunctional oxetane compound

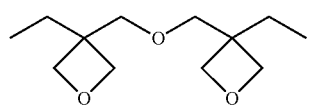

(compound a)

is used in combination with an epoxy compound leading to an improvement in the balance between adhesiveness and durability. Japanese Patent No. JP4003264B2 discloses a bifunctional oxetane compound which can improve the curing speed of a cationic curing system. Therefore, much attention has been paid to the multi-functionalization of oxetane-based monomers in many fields of application, for example fields of adhesives, sealants, encapsulants, and the like, and particularly those used in members and components of LED devices. This is also the trend in the development of oxetane-based cation polymerizable monomers. However, with respect to current polyfunctional oxetane-based monomers, there are still disadvantages, such as it is difficult to obtain a good balance among hardness, flexibility, adherence, and/or the like of a cured product after use, and overall properties still need to be further improved.

In some embodiments, the disclosed polyfunctional oxetane-based compound has higher reactivity and better application properties. Some methods for producing the disclosed polyfunctional oxetane-based compound are disclosed. When these polyfunctional oxetane-based cation polymerizable monomers are used in combination with an epoxy compound, the curing speed is high, and the cured product has excellent hardness, flexibility, adherence, and heat resistance.

In at least some embodiments, a polyfunctional oxetane-based compound can have a structure represented by general formula (I):

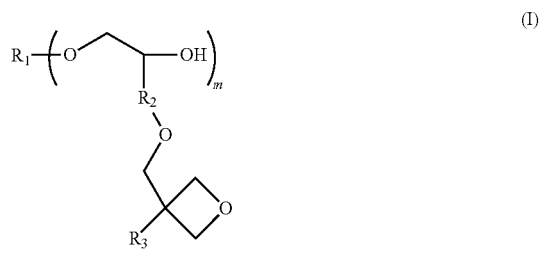

wherein, $R_1$ represents a $C_1$-$C_{40}$ linear or branched m-valent alkyl group, a $C_2$-$C_{20}$ m-valent alkenyl group, or a $C_6$-$C_{40}$ m-valent aryl group, wherein —$CH_2$— can be optionally substituted with an oxygen atom, —NH—, or

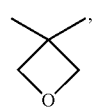

provided that two —O-'s are not directly connected; and optionally, one or more hydrogen atoms in these groups can be independently substituted with a group selected from an alkyl group, a halogen, and a nitro group; $R_2$ represents a $C_1$-$C_{20}$ linear or branched alkylene group, wherein —$CH_2$— in the main chain can be optionally substituted with an oxygen atom, provided that two —O-'s are not directly connected, and optionally, one or more hydrogen atoms in (compound b)

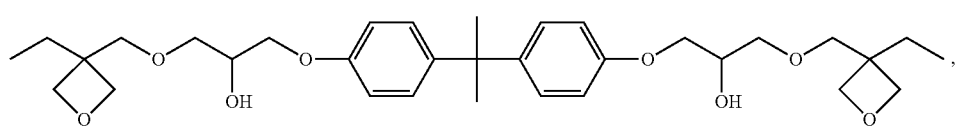

the group can be each independently substituted with a group selected from an alkyl group, a halogen, and a nitro group; $R_3$ represents hydrogen, a halogen, a nitro group, a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_2$-$C_{10}$ alkenyl group, or a $C_6$-$C_{20}$ aryl group, and optionally, one or more hydrogen atoms in these groups can be each independently substituted with a group selected from an alkyl group, a halogen, and a nitro group; and m represents an integer of 1-8.

In at least some preferred embodiments, the compound of general formula (I) contains two or more oxetanyl groups. To this end, m is suitably selected to be a numeric value of 2 or more; or when m=1, $R_1$ should contain at least one oxetanyl group.

In at least some preferred embodiments, $R_1$ represents a $C_1$-$C_{40}$ linear or branched co-valent alkyl group, a $C_2$-$C_{10}$ linear or branched m-valent alkenyl group, or a $C_6$-$C_{30}$ m-valent aryl group, wherein —$CH_2$— can be optionally substituted with an oxygen atom, —NH—, or

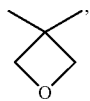

provided that two —O—'s are not directly connected; and optionally, one or more hydrogen atoms in these groups can be independently substituted with a group selected from an alkyl group, a halogen, and a nitro group.

Exemplarily, $R_1$ can be selected from the following structures: a $C_1$-$C_{12}$ linear or branched 1-to-4-valent alkyl group, a $C_2$-$C_6$ linear or branched 1-to-4-valent alkenyl group,

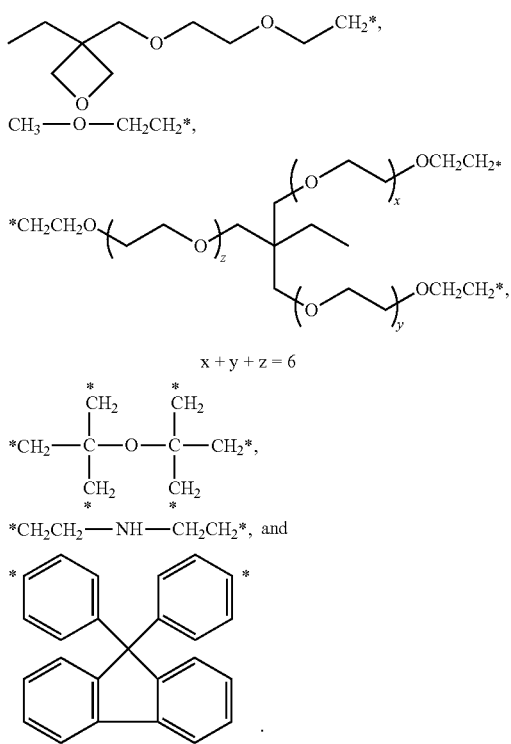

In at least some preferred embodiments, $R_2$ represents a $C_1$-$C_{10}$ linear or branched alkylene group, wherein —$CH_2$— in the main chain can be optionally substituted with an oxygen atom, provided that two —O—'s are not directly connected. Further preferably, $R_2$ represents a $C_1$-$C_6$ linear or branched alkylene group, wherein —$CH_2$— in the main chain can be optionally substituted with an oxygen atom, provided that two —O—'s are not directly connected.

In at least some preferred embodiments, $R_3$ represents hydrogen, a $C_1$-$C_{10}$ linear or branched alkyl group, a $C_3$-$C_{10}$ cycloalkyl group, a $C_4$-$C_{10}$ cycloalkylalkyl group, a $C_4$-$C_{10}$ alkylcycloalkyl group, a $C_2$-$C_5$ alkenyl group, or a phenyl group. Further preferably, $R_3$ represents a $C_1$-$C_4$ linear or branched alkyl group, or a $C_4$-$C_5$ cycloalkylalkyl group.

In at least some preferred embodiments, m is an integer of 1-6, more preferably an integer of 1-4.

Unless otherwise specified, related terms have the meanings as commonly understood in the art. A range of a numeric value includes endpoint values and all point values between the endpoint values. For example, "$C_1$-$C_{10}$" includes $C_1$, $C_2$, $C_3$, $C_4$, $C_5$, $C_6$, $C_7$, $C_8$, $C_9$, and $C_{10}$, and "an integer of 1-4" includes 1, 2, 3, and 4.

A production method of the polyfunctional oxetane-based compound represented by general formula (I) described above, can comprise: performing a reaction in the presence of a catalyst by using the hydroxy-containing compound represented by general formula (II) and an oxetanyl-containing epoxy compound represented by general formula (III) as raw materials to obtain a product, wherein a reaction formula is as follows:

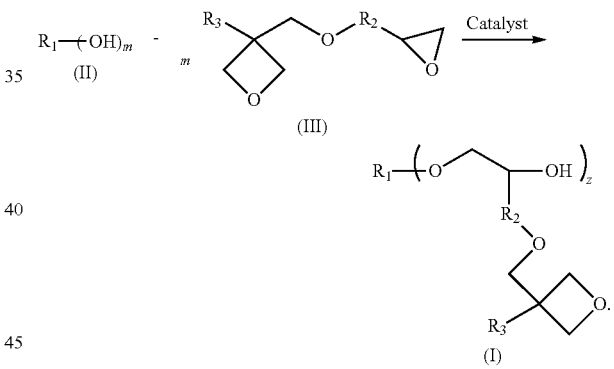

In the production method described above, the catalyst used can be: an alkali metal hydroxide, such as sodium hydroxide, potassium hydroxide, and the like; an alkali metal salt of an alcohol, such as sodium methoxide, potassium ethanoxide, sodium tert-butoxide, and the like; an alkali metal carbonate, such as sodium carbonate, potassium carbonate, and the like; an alkali metal bicarbonate, such as sodium bicarbonate, potassium bicarbonate, and the like; an alkyl metal lithium compound, such as butyl lithium, phenyl lithium, and the like; and a lithium amide compound, such as a lithium diisopropylamide, lithium hexamethyldisilyl amide, and the like. The usage amount of the catalyst can be easily determined. In at least some preferred embodiments, the usage amount of the catalyst is 0.1-20% of the molar amount of the compound of general formula (II). In at least some more preferred embodiments, the usage amount of the catalyst 1-20% of the molar amount of the compound of general formula (II).

According to the types of the raw materials, the reaction system can optionally comprise an organic solvent. The type of the solvent suitably used is not particularly limited, as long as it can dissolve the raw materials of the reaction and do not influence, or at least overly influence, the reaction. For example, it can be: a nitrile solvent, such as acetonitrile, propionitrile, benzonitrile, and the like; an amide solvent, such as N,N-dimethylformamide, N,N-dimethylacetamide, N-methylpyrrolidone, and the like; an ether solvent, such as tetrahydrofuran, dioxane, and the like; and an aromatic solvent, such as benzene, toluene, xylene, and the like. These solvents can be used alone or used by mixing two or more thereof, and the total usage amount can be properly adjusted according to the uniformity and the stirring property of the reaction system. This will be easily determined.

In at least some embodiments, the reaction temperature can be varied according to the types of the raw materials, and is typically 25-200° C., preferably 50-150° C. The reaction pressure is not particularly limited, and is typically atmospheric pressure.

After completion of the reaction, the pH value is adjusted to neutral, and filtration, water washing, extraction, and reduced-pressure distillation are performed to obtain the polyfunctional oxetane-based compound represented by general formula (I).

A cation polymerizable monomer can be generated by a reaction of the polyfunctional oxetane-based compound represented by general formula (I) described above and epichlorohydrin, having a structure represented by general formula (IV):

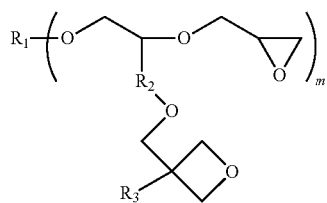

(IV)

wherein $R_1$, $R_2$, $R_3$, and m have the same definitions as those in general formula (I).

The production method of the cation polymerizable monomer represented by general formula (IV) comprises: performing a reaction between a polyfunctional oxetane-based compound represented by general formula (I) and epichlorohydrin under a basic condition; wherein a reaction formula is as follows:

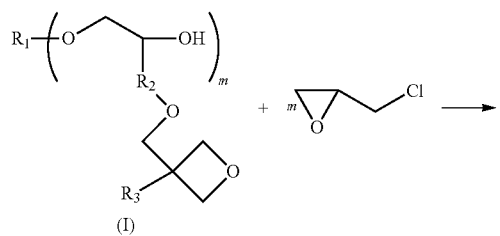

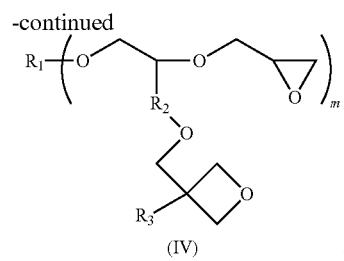

(IV)

In the production method of the cation polymerizable monomer represented by general formula (IV), the establishment of basic conditions will be easily conceived. Exemplarily, a basic compound can be added to the reaction system, for example, an alkali metal hydroxide, such as sodium hydroxide, potassium hydroxide, and the like; an alkali metal carbonate, such as sodium carbonate, potassium carbonate, and the like; and an alkali metal bicarbonate, such as sodium bicarbonate, potassium bicarbonate, and the like. The basic compound can promote the reaction to be performed smoothly, and the usage amount thereof can be easily determined. In at least some preferred embodiments, the usage amount of the basic compound is 1-20 times, more preferably m-10 times, of the molar amount of the compound of general formula (I).

Optionally, an organic solvent can be selectively used as a support medium in the reaction system according to the types of the raw materials. The type of the solvent suitably used is not particularly limited, as long as it can dissolve the raw materials of the reaction and do not influence, or at least overly influence, the reaction. For example, it can be: a nitrile solvent, such as acetonitrile, propionitrile, benzonitrile, and the like; an amide solvent, such as N,N-dimethylformamide, N,N-dimethylacetamide, N-methylpyrrolidone, and the like; an ether solvent, such as tetrahydrofuran, dioxane, and the like; and an aromatic solvent, such as benzene, toluene, xylene, and the like. These solvents can be used alone or used by mixing two or more thereof. The reaction temperature can be varied according to the types of the raw materials, and is typically 25-120° C., preferably 30-80° C. After completion of the reaction, a product can be obtained by water washing, extraction, and reduced-pressure distillation.

A cation polymerizable monomer, can be formed by performing a reaction between the compound represented by general formula (I) described above and an ester compound represented by general formula (V), $$R_4(\text{—COOR}_5)_n \qquad (V)$$

wherein $R_4$ represents a n-valent linking group, $R_5$ represents a $C_1$-$C_{10}$ linear or branched alkyl group, and n represents an integer of 1-8; provided that the cation polymerizable monomer has at least two oxetanyl groups.

According to different values selected for m and n, this cation polymerizable monomer can be a cation polymerizable monomer obtained by a reaction between a compound of general formula (I) having one hydroxy group (i.e., m=1) and a compound having one ester group (i.e., n=1, and $R_1$ in the compound of general formula I contains at least one oxetanyl group at this point) or a compound having a plurality of ester groups (i.e., n>1), or can be a cation polymerizable monomer obtained by a reaction between a compound of general formula (I) having a plurality of hydroxy groups (i.e., m>1) and a compound having one ester group or a compound having a plurality of ester groups.

In at least some preferred embodiments, in the ester compound represented by general formula (V), $R_4$ represents a $C_1$-$C_{20}$ linear or branched n-valent alkyl group, a $C_2$-$C_{20}$ n-valent alkenyl group, a $C_3$-$C_{20}$ n-valent cycloalkyl group, a $C_4$-$C_{20}$ n-valent cycloalkylalkyl group, a $C_4$-$C_{20}$ n-valent alkylcycloalkyl group, or a $C_6$-$C_{40}$ n-valent aryl group; optionally, —$CH_2$— in these groups can be substituted with an oxygen atom or a 1,4-phenylene group, provided that two —O-'s are not directly connected; and optionally, one or more hydrogen atoms in these groups can be independently substituted with a group selected from an alkyl group, a halogen, and a nitro group.

In at least some preferred embodiments, $R_4$ represents a $C_1$-$C_{10}$ linear or branched n-valent alkyl group, a $C_2$-$C_{10}$ n-valent alkenyl group, a $C_3$-$C_{10}$ n-valent cycloalkyl group, a $C_4$-$C_{10}$ n-valent cycloalkylalkyl group, a $C_4$-$C_{10}$ n-valent alkylcycloalkyl group, or a $C_6$-$C_{20}$ n-valent aryl group; and optionally, —$CH_2$— in these groups can be substituted with an oxygen atom or a 1,4-phenylene group, provided that two —O-'s are not directly connected.

In at least some more preferred embodiments, $R_4$ represents a $C_1$-$C_8$ linear or branched n-valent alkyl group, a $C_7$-$C_{12}$ n-valent aryl group, or a n-valent phenyl group.

In at least some preferred embodiments, in the ester compound described above, $R_5$ is selected from a $C_1$-$C_4$ linear or branched alkyl group, particularly a methyl group and an ethyl group.

In at least some preferred embodiments, n is an integer of 1-4.

Exemplarily, the ester compound represented by general formula (V) is selected from the following compounds, but is not limited to these compounds:

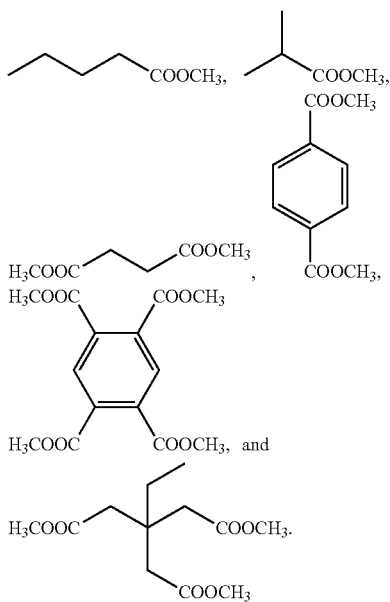

In at least some embodiments, the production method of the cation polymerizable monomer described above comprises: performing a transesterfication reaction between the polyfunctional oxetane-based compound represented by general formula (I) and the ester compound represented by general formula (V) in the presence of a catalyst.

In at least some preferred embodiments, catalyst used in the reaction is a titanate-based compound, more preferably one or a combination of two or more of 2-ethylhexyl titanate, tetramethyl titanate, tetraethyl titanate, tetraisopropyl titanate, tetrabutyl titanate, tetraisobutyl titanate, and the like. The usage amount of the catalyst can be easily determined. In some preferred embodiments, the usage amount of the catalyst is 0.05-5 wt % of the compound of general formula (I). In some more preferred embodiments, the usage amount of the catalyst is 0.1-2 wt % of the compound of general formula (I).

In at least some preferred embodiments, the reaction system comprises an organic solvent as a support medium. The type of the solvent suitably used is not particularly limited, as long as it can dissolve the raw materials of the reaction and do not influence, or at least overly influence, the reaction, such as benzene, toluene, xylene, and the like. The usage amount of the solvent can be properly adjusted according to the uniformity and the stirring property of the reaction system. This can be easily determined.

The reaction temperature can be varied according to the types of the raw materials. In at least some preferred embodiments, the reaction temperature is typically 0-200° C., preferably 50-150° C. In some embodiments, after completion of the reaction, a product is obtained by water washing, filtration, and reduced-pressure distillation.

In at least some embodiments, a cation polymerizable monomer, can be formed by performing a reaction between the compound represented by general formula (I) described above and an isocyanate compound represented by general formula (VI),

wherein $R_6$ represents a p-valent linking group, and p represents an integer of 1-8; provided that the cation polymerizable monomer has at least two oxetanyl groups.

In at least some embodiments, according to different values selected for m and p, this cation polymerizable monomer can be a cation polymerizable monomer obtained by a reaction between a compound of general formula (I) having one hydroxy group (i.e., m=1) and a compound having one isocyanate radical (i.e., p=1, and $R_1$ in the compound of general formula I contains at least one oxetanyl group at this point) or a compound having a plurality of isocyanate radicals (i.e., p>1), or can be a cation polymerizable monomer obtained by a reaction between a compound of general formula (I) having a plurality of hydroxy groups (i.e., m>1) and a compound having one isocyanate radical or a compound having a plurality of isocyanate radicals.

In at least some preferred embodiments, in the isocyanate compound represented by general formula (VI), $R_6$ represents a $C_1$-$C_{20}$ linear or branched p-valent alkyl group, a $C_2$-$C_{20}$ p-valent alkenyl group, a $C_3$-$C_{20}$ p-valent cycloalkyl group, a $C_4$-$C_{20}$ p-valent cycloalkylalkyl group, a $C_4$-$C_{20}$ p-valent alkylcycloalkyl group, or a $C_6$-$C_{40}$ p-valent aryl group; optionally, —$CH_2$— in these groups can be substituted with an oxygen atom or a 1,4-phenylene group, provided that two —O-'s are not directly connected; and optionally, one or more hydrogen atoms in these groups can be independently substituted with a group selected from an alkyl group, a halogen, and a nitro group.

In some preferred embodiments, $R_6$ represents a $C_1$-$C_{10}$ linear or branched p-valent alkyl group, a $C_2$-$C_{10}$ p-valent alkenyl group, a $C_3$-$C_{10}$ p-valent cycloalkyl group, a $C_4$-$C_{10}$ p-valent cycloalkylalkyl group, a $C_4$-$C_{10}$ p-valent alkylcycloalkyl group, or a $C_6$-$C_{20}$ p-valent aryl group; optionally, —$CH_2$— in these groups can be substituted with an oxygen atom or a 1,4-phenylene group, provided that two —O-'s are not directly connected; and optionally, one or more hydrogen atoms in these groups can be independently substituted with an alkyl group.

In some more preferred embodiments, $R_6$ represents a $C_1$-$C_8$ linear or branched p-valent alkyl group, or a $C_6$-$C_{12}$ p-valent aryl group; optionally, —$CH_2$— in these groups can be substituted with an oxygen atom or a 1,4-phenylene group, provided that two —O-'s are not directly connected; and optionally, one or more hydrogen atoms in these groups can be independently substituted with a $C_1$-$C_4$ alkyl group. In some preferred embodiments, p is an integer of 1-4.

Exemplarily, the isocyanate compound represented by general formula (VI) is selected from the following compounds, but is not limited to these compounds:

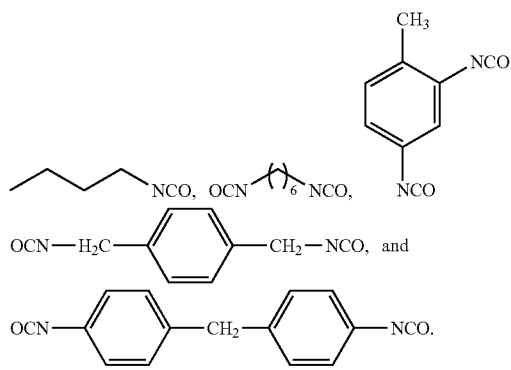

In at least some embodiments, the production method of the cation polymerizable monomer described above comprises: performing a reaction between the polyfunctional oxetane-based compound represented by general formula (I) and the isocyanate compound represented by general formula (VI) in the presence of a catalyst.

The catalyst used in the reaction and usage amount thereof can be easily determined. In some preferred embodiments, the catalyst is dibutyltin laurate, and the usage amount thereof is 0.05-5 wt % of the compound of general formula (I). In some more preferred embodiments, the usage amount is 0.1-2 wt % of the compound of general formula (I).

Optionally, an organic solvent can be selectively used as a support medium in the reaction system according to the types of the raw materials. The type of the solvent suitably used is not particularly limited, as long as it can dissolve the raw materials of the reaction and do not influence, or at least overly influence, the reaction. For example, it can be: a nitrile solvent, such as acetonitrile, propionitrile, benzonitrile, and the like; an amide solvent, such as N,N-dimethylformamide, N,N-dimethylacetamide, N-methylpyrrolidone, and the like; an ether solvent, such as tetrahydrofuran, dioxane, and the like; and an aromatic solvent, such as benzene, toluene, xylene, and the like. These solvents can be used alone or used by mixing two or more thereof. The usage amount of the solvent can be properly adjusted according to the uniformity and the stirring property of the reaction system. This can be easily determined.

The reaction temperature can be varied according to the types of the raw materials. In some embodiments, the reaction temperature is 0-100° C., preferably 20-80° C.

In some embodiments, products obtained by a reaction of the polyfunctional oxetane-based compound represented by general formula (I) and epichlorohydrin, the ester compound represented by general formula (V), or the isocyanate compound represented by general formula (VI) are polyfunctional oxetane-based compounds, which can exhibit properties similar to or better than those of the compound of general formula (I). In some embodiments, a new functional group can be introduced into the general formula (I) by the reaction so as to adjust properties, and thus application uses.

DETAILED DESCRIPTION OF ILLUSTRATIVE EMBODIMENT(S)

It is to be indicated that the described Examples and features in the Examples can be combined with each other without being conflicted. The Examples are not to be construed as limiting.

PREPARATION EXAMPLES

Example 1

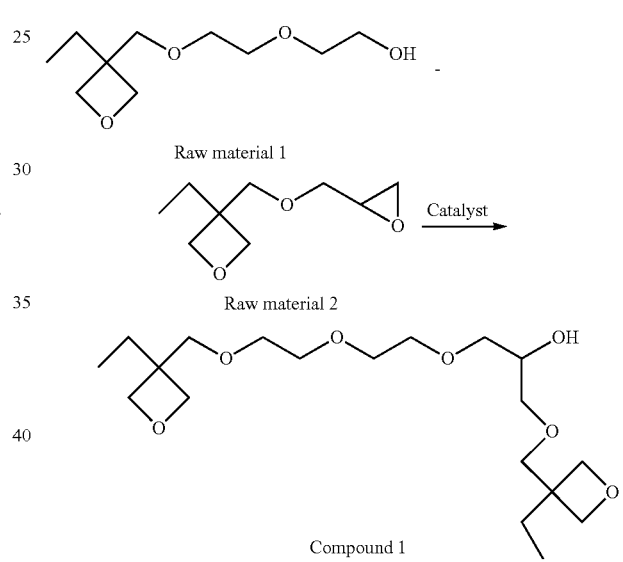

In an example embodiment, 102 g (0.5 mol) of the raw material 1, 4 g (0.1 mol) of sodium hydroxide, and 100 g of toluene were sequentially added to a 250 ml four-neck flask mounted with a stirring apparatus, a thermometer, and a reflux condenser tube, and the temperature was increased to 80° C. with stirring. 86 g (0.5 mol) of the raw material 2 was dropped within 1.5 h, and a reaction was continued with stirring. Vapor phase tracking was performed until the content of the raw material 1 did not change anymore, and heating was stopped. The pH was adjusted to neutral, and filtration, water washing, extraction, and reduced-pressure distillation were performed to obtain 174 g of a light yellow viscous liquid.

The structure of the product, i.e., compound 1, was confirmed by GC-MS and $^1$H-NMR.

MS (m/e): 376 (M);

$^1$H-NMR (CDCl$_3$, 500 MHz): δ0.96 (6H, m), δ1.25 (4H, s), δ2.01 (1H, d), δ3.29 (4H, s), δ3.52-3.54 (12H, m), δ3.87 (1H, m), δ4.65 (8H, s).

Example 2

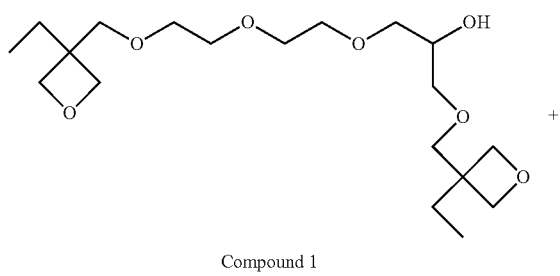

Compound 1

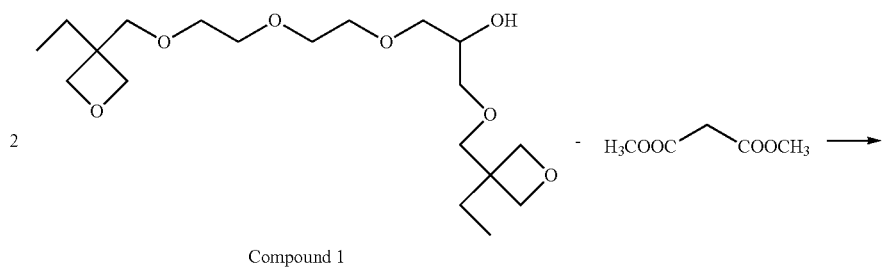

Compound 1

-continued

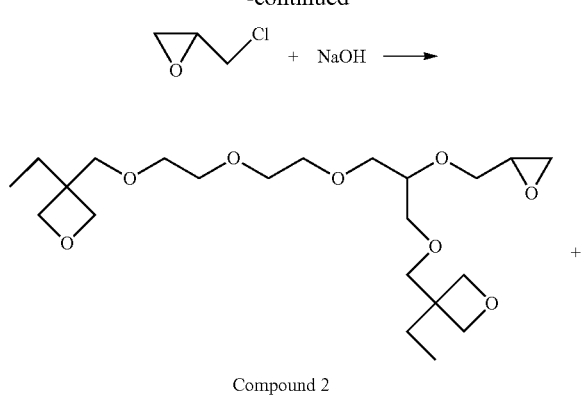

Compound 2

In an example embodiment, 188 g (0.5 mol) of compound 1, 46 g (0.5 mol) of epichlorohydrin, and 20 g (0.5 mol) of sodium hydroxide were sequentially added to a 250 ml four-neck flask mounted with a stirring apparatus, a thermometer, and a reflux condenser tube, and a reaction was performed at 40° C. for 12 h. Vapor phase tracking was performed until compound 1 completely disappeared. After completion of the reaction, water washing, extraction, and reduced-pressure distillation were performed to finally obtain 198.7 g of a colorless viscous liquid The structure of the product, i.e., compound 2, was confirmed by GC-MS and $^1$H-NMR.

MS (m/e): 432 (M);

$^1$H-NMR (CDCl$_3$, 500 MHz): δ0.96 (6H, m), δ1.25 (4H, s), δ2.50 (2H, d), δ2.86 (1H, m), δ3.29 (4H, s), δ3.49-3.54 (15H, m), δ4.65 (8H, s).

Example 3

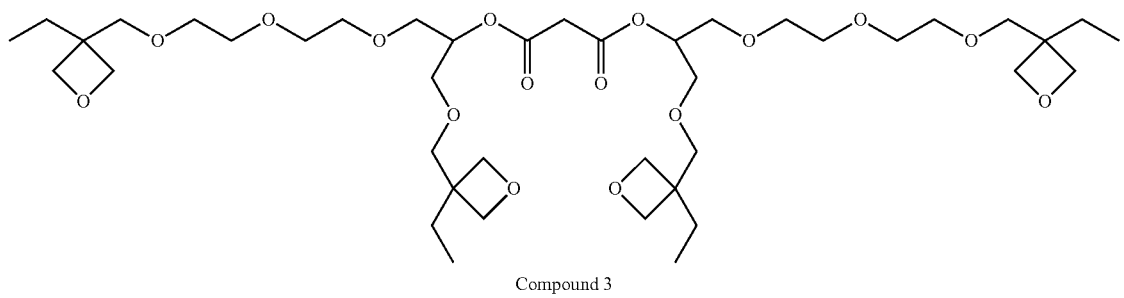

Compound 3

2 CH$_3$OH

In an example embodiment, 188 g (0.5 mol) of compound 1, 33 g (0.25 mol) of dimethyl malonate, and 200 g of toluene were added to a four-neck flask mounted with a stirring apparatus, a thermometer, a rectification column, and a water trap apparatus, and moisture in the system was removed with heating reflux. After cooling down to about 60° C., 2.5 g of tetraethyl titanate was added, a reaction was performed with heating reflux, and the reflux ratio was adjusted to bring out methanol generated in the reaction. When the temperature at the top of the rectification column was increased to 110° C., the reaction was stopped, and the temperature was decreased to 70° C. 10 g of water was added with stirring for 1 h, filtration was performed while it is hot, and the filtrate was subjected to reduced-pressure distillation to obtain 197 g of a light-yellow viscous liquid.

The structure of the product, i.e., compound 3, was confirmed by GC-MS and $^1$H-NMR.

MS (m/e): 821 (M);

$^1$H-NMR (CDCl$_3$, 500 MHz): δ0.96 (12H, m), δ1.25 (8H, m), δ3.21 (2H, s), δ3.29 (8H, s), δ3.54-3.61 (24H, m), δ4.61-4.65 (18H, m).

Example 4

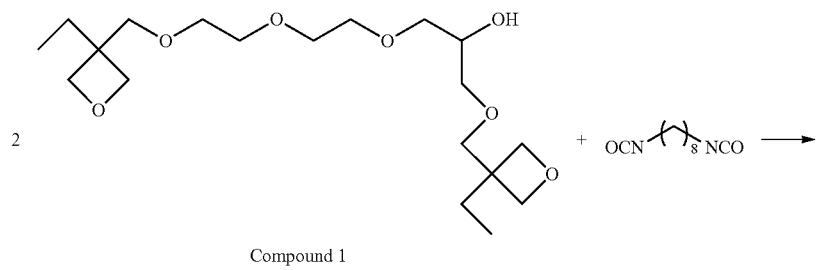

Compound 1

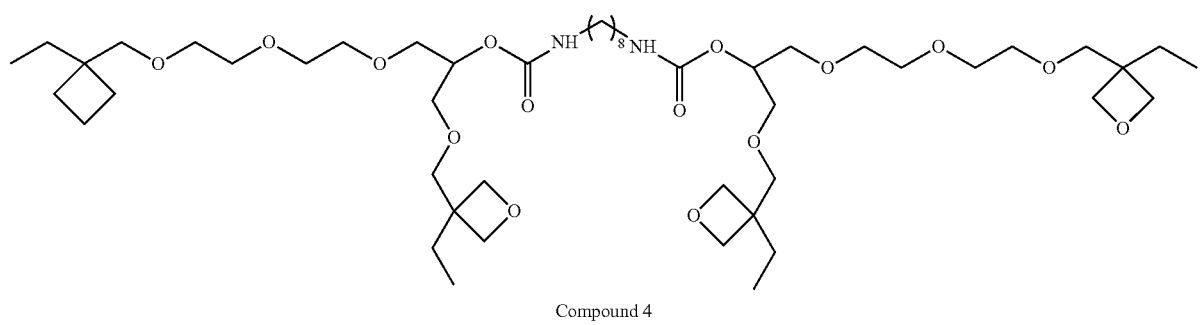

Compound 4

In an example embodiment, 188 g (0.5 mol) of compound 1 and 0.1 g of dibutyltin laurate were added to a four-neck flask mounted with a stirring apparatus and a thermometer. The temperature was controlled at about 40° C., and 42 g (0.25 mol) of hexamethylene diisocyanate was dropped. After the dropping, a reaction was performed with maintaining the temperature, and the reaction was finished when the NCO value was decreased to 0.05% or less.

The structure of the product, i.e., compound 4, was confirmed by GC-MS and $^1$H-NMR.

MS (m/e): 920 (M);

$^1$H-NMR (CDCl$_3$, 500 MHz): δ0.96 (12H, m), δ1.25-1.55 (16H, m), δ3.29 (8H, s), δ3.54-3.61 (24H, m), δ4.61-4.65 (18H, m), δ8.0 (2H, m).

Example 5

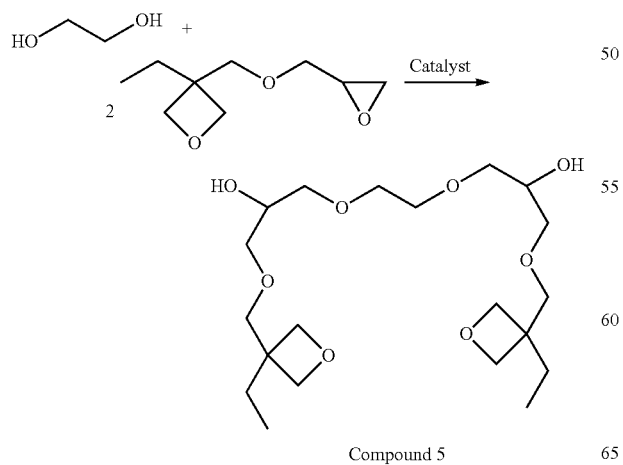

Compound 5

Compound 5 was produced with reference to the process of Example 1, and its structure was confirmed by GC-MS and $^1$H-NMR.

MS (m/e): 406 (M);

$^1$H-NMR (CDCl$_3$, 500 MHz): δ0.96 (6H, m), δ1.25 (4H, s), δ2.01 (2H, d), δ3.29 (4H, s), δ3.52-3.54 (12H, m), δ3.87 (2H, m), δ4.65 (8H, s).

Example 6

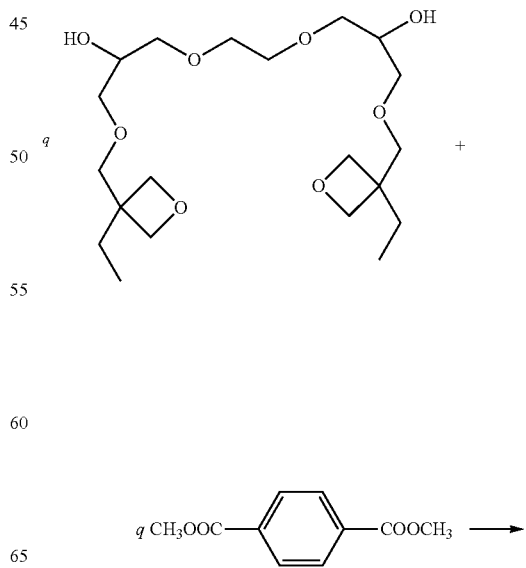

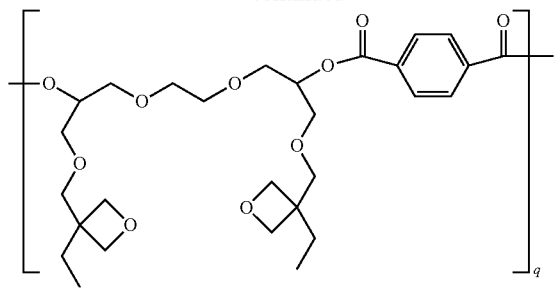

Compound 6

2qCH₃OH

Compound 6 was produced from compound 5 with reference to the process of Example 3.

The structure of compound 6 was confirmed by IR.

IR (KBr), ν/cm-1: 981 (s,

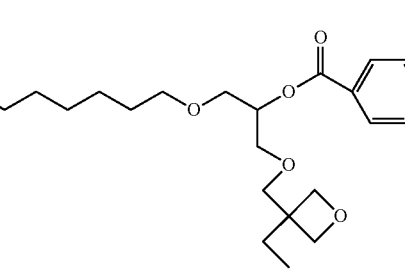), 1200 (m, C—O—C), 1720 (s, C=O), 960.7 (m, Ar—H).

Example 7

Products 7-13 having structures as shown in Table 1 were synthesized by using corresponding agents with reference to the methods of Examples 1-6.

TABLE 1

| Compound | Structure | 1H-NMR/IR |
|---|---|---|
| 7 | 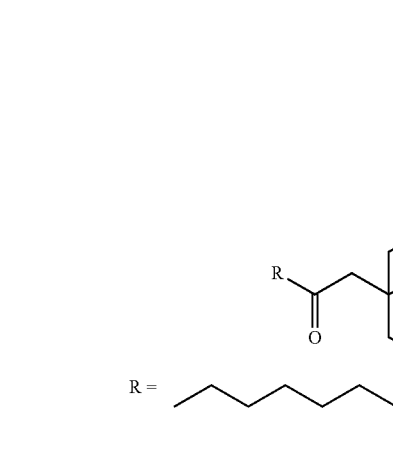 | δ 0.96 (12H, m)<br>δ 1.25-1.46 (28H, m)<br>δ 3.29-3.79 (16H, m)<br>δ 4.61-4.65 (10H, m)<br>δ 8.1 (4H, d) |
| 8 | 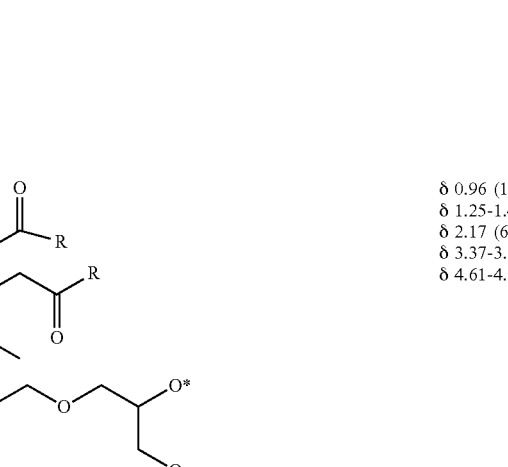 | δ 0.96 (15H, m)<br>δ 1.25-1.46 (44H, m)<br>δ 2.17 (6H, m)<br>δ 3.37-3.61 (36H, m)<br>δ 4.61-4.65 (15H, m) |

TABLE 1-continued
| Compound | Structure | 1H-NMR/IR |
|---|---|---|
| 9 | 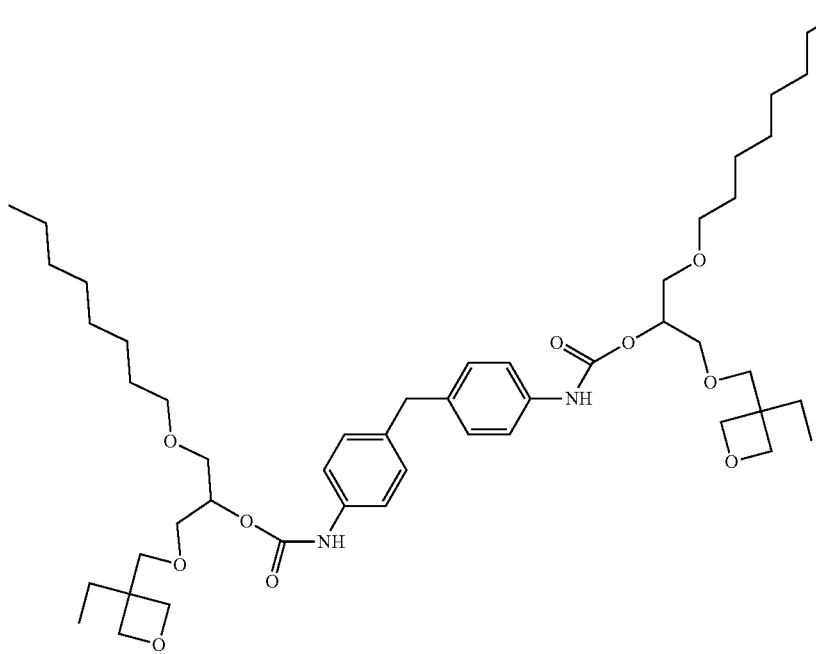 | δ 0.96 (12H, m)<br>δ 1.25-1.46 (28H, m)<br>δ 3.37-3.81 (18, m)<br>δ 4.61-4.65 (10H, m)<br>δ 7.04-7.52 (8H, m)<br>δ 8.0 (2H, s) |
| 10 | 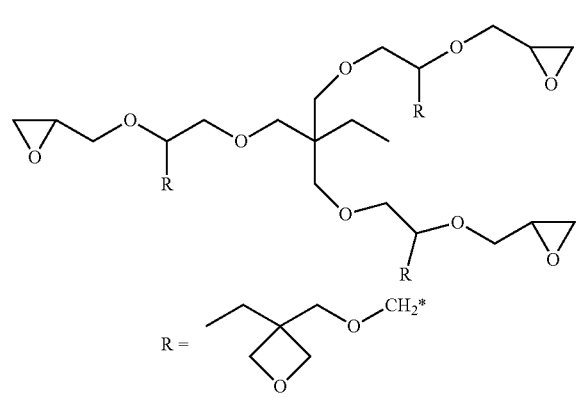 | δ 0.96-1.25 (20H, m)<br>δ 2.50-2.86 (9H, m)<br>δ 3.29-3.50 (33, m)<br>δ 4.65 (12H, s) |
| 11 | <br>$x + y + z = 6$ | 913 (s, 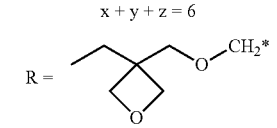)<br>981 (s, )<br>1200 (m, C—O—C) |

TABLE 1-continued

| Compound | Structure | 1H-NMR/IR |
|---|---|---|
| 12 | (structure shown) x + y + z = 6; R = (oxetane group) | 981 (s, oxetane); 1200 (m, C—O—C); 1720 (s, C=O) |
| 13 | (structure shown) | δ 0.96 (12H, m); δ 1.25-1.55 (12H, m); δ 2.96 (4, m); δ 3.29-4.65 (22H, m); δ 6.65-8.0 (18H, m) |

Test of Properties

By formulating exemplary photocurable compositions, various application properties of the polyfunctional oxetane-based monomer were evaluated, including aspects of curing speed, hardness, flexibility, adherence, heat resistance, and the like.

In the process of the test, TTA21 and E-51 were representative of epoxy monomers, PAG-202 was representative of a cationic photoinitiator, and the compounds a and/or b described in the background art were used as comparative polyfunctional oxetane-based monomers.

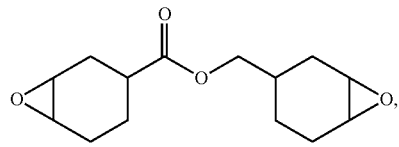
TTA21

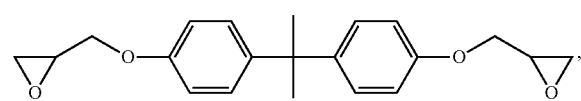
E-51

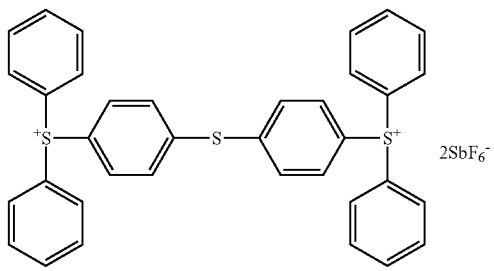
PAG-202

1. Test of Curing Speed

In an example embodiment, raw materials were formulated according to parts by mass as shown in Table 2 and then evenly mixed in a dark room, and about 1 mg of a sample was weighed and spread in an aluminum crucible. The sample was scanned and cured by using a Perkin Elmer differential scanning calorimeter (DSC8000) equipped with an ultraviolet light source of a mercury arc lamp (Omni-Cure-S2000).

The time when the maximal curing heat release was induced by UV and the time required for achieving 90% of UV curing heat release were recorded. A shorter time when the peak was reached and a shorter time when 90% conversion was achieved were indications of good curing properties. Test results are summarized in Table 2.

TABLE 2

|  | 1# | 2# | 3# | 4# | 5# | 6# | 7# | 8# | 9# | 10# |
|---|---|---|---|---|---|---|---|---|---|---|
| PAG202 | 2 | 2 | 2 | 2 | 2 | 2 | 2 | 2 | 2 | 2 |
| TTA21 | 49 | 49 | 49 | 49 | 49 | — | — | — | — | — |
| E-51 | — | — | — | — | — | 49 | 49 | 49 | 49 | 49 |
| Compound 2 | 49 | — | — | — | — | 49 | — | — | — | — |
| Compound 3 | — | 49 | — | — | — | — | 49 | — | — | — |
| Compound 8 | — | — | 49 | — | — | — | — | 49 | — | — |
| Compound 10 | — | — | — | 49 | — | — | — | — | 49 | — |
| Compound b | — | — | — | — | 49 | — | — | — | — | 49 |
| Time when the peak is reached/min | 0.12 | 0.08 | 0.10 | 0.09 | 0.16 | 0.38 | 0.20 | 0.33 | 0.25 | 0.68 |
| Time when 90% is achieved/min | 1.15 | 0.96 | 1.05 | 1.04 | 1.32 | 3.25 | 2.42 | 3.06 | 2.90 | 4.58 |

As can be seen from Table 2, after the disclosed polyfunctional oxetane-based monomer was used in combination with an epoxy monomer in a cationic photocuring system, it had a high curing speed and was superior to an existing compound having the same type of structure, i.e., compound b.

2. Test of Properties after Film-Forming by Curing

The polyfunctional oxetane-based monomers of this disclosed or compounds a and b each was mixed with an epoxy monomer TTA21 at a mass ratio of 1:1, and 2% of an initiator PAG-202 was further added. After evenly stirring and mixing in a dark room, formulations were coated onto a sand paper-polished tin-plated steel sheet substrates with 25# wire bar to obtain coating layers having a thickness of about 25 μm. The formulations were then placed in a track type exposure machine (RW-UV.70201) and completely exposed 10 times, wherein each exposure was 80 mj/cm2. The test was then performed after standing for 24 h.

(1) Test of Hardness

Cured films were tested under conditions of a temperature of 23° C. and a relative humidity of 50%. The evaluation method for pencil hardness specified in GB/T 6739-2006 was used as a standard. A pencil was inserted into a test instrument, fixed with a clip, and maintained to be horizontal. The tip of the pencil was placed on the surface of a paint film, and was pushed by a distance of at least 7 mm at a speed of 1 mm/s toward a direction departing from yourself. If no scratch occurred, an experiment was repeated in an untested area by replacing with a pencil having a higher hardness, until a scratch having a length of at least 3 mm occurred. The hardness of the coating layer was represented by the hardness of hardest pencil which did not allow the occurrence of scratch on the coating layer.

(2) Test of Flexibility

Cured films were tested under conditions of a temperature of 23° C. and a relative humidity of 70%. On the basis of the test method of the flexibility of paint films in GB/T1731-93, the outside of a tin-plated steel plate coated with a cured coating layer was sequentially wound onto 10-, 5-, 4-, 3-, 2-, and 1-millimeter rod shafts along the length direction and bent for 2-3 s. By observing with a magnifier, the flexibility of the ultraviolet photocured coating layer was represented by the diameter of the rod shaft having the smallest damage of the coating layer.

(3) Test of Adherence

Cured films were tested under conditions of a temperature of 23° C. and a relative humidity of 50%. The evaluation method for paint film crosscut specified in GB/T 9286-1998 was used as a standard. A coating film was cut into one hundred grids. The tip of the cutter was required to scratch the substrate and to be sharp, and the angle formed between the tip of the cutter and the coating film was 45 degrees. Paint scraps were brushed off with a soft brush, a 3M adhesive tape was stuck onto the one hundred grids, and a force was applied to allow the adhesive tape to be firmly stuck onto the surface of the coating film and the crosscut parts. Within 2 min, one end of the 3M adhesive tape was held firmly to form an angle of 60 degrees, and the adhesive tape was steadily peeled off in 1 second. The evaluation was performed according to the criteria described below.

Grade 0: Cut edges were completely smooth and nothing fell off;

Grade 1: A few parts of the coating layer fell off at the intersections of cuts, but the influenced crosscut area could not be significantly greater than 5%;

Grade 2: Parts of the coating layer fell off at the intersections of cuts and/or along the edges of cuts, and the influenced crosscut area was significantly greater than 5% but could not be significantly greater than 15%;

Grade 3: The coating layer fell off partly or completely in the form of large fragments along the cut edges and/or fell off partly or completely on different parts of the grids, and the influenced crosscut area was significantly greater than 15% but could not be significantly greater than 35%;

Grade 4: The coating layer fell off in the form of large fragments along the cut edges and/or some grids fell off partly or completely, and the influenced crosscut area was significantly greater than 35% but could not be significantly greater than 65%;

Grade 5: The degree of falling-off exceeded Grade 4.

(4) Test of Glass Transition Temperature

A test was performed on the cured film by using a differential scanning calorimeter (PE DSC8000) under a test condition as follows: under a nitrogen atmosphere, the temperature was increased from −20° C. to 200° C. at a rate of 10° C./min and maintained at 200° C. for 1 min, then decreased from 200° C. to −20° C. at a rate of 10° C./min and maintained at −20° C. for 1 min, and increased from −20° C. to 200° C. at a rate of 10° C./min, so that the glass transition temperature Tg (° C.) was measured.

(5) Test of Thermal Decomposition Temperature

A thermogravimetric analysis was performed on the cured film by using a thermogravimetric analyzer (PE STA6000). The temperature of a part, where a tangent line of a part where the weight was not decreased or was gradually decreased and a tangent line of an inflection point where the weight was rapidly decreased were intersected, was taken as a thermal decomposition temperature T (° C.). The evaluation was performed according to the criteria described below.

A thermal decomposition temperature T (° C.) at 300 or more was denoted by: Δ;

A thermal decomposition temperature T (° C.) at 250-300 or more was denoted by: ○; and A thermal decomposition temperature T (° C.) at 250 or less was denoted by: x.

Evaluation results were summarized in Table 3.

TABLE 3

| | Compound | Hardness | Flexibility | Adherence | Tg (° C.) | Heat Resistance |
|---|---|---|---|---|---|---|
| Disclosed Compounds | Compound 3 | 4H | 1 | Grade 0 | 96 | ○ |
| | Compound 6 | 4H | 1 | Grade 0 | 128 | Δ |
| | Compound 8 | 4H | 2 | Grade 0 | 115 | Δ |
| | Compound 10 | 4H | 2 | Grade 0 | 109 | Δ |
| | Compound 12 | 4H | 1 | Grade 0 | 132 | Δ |
| | Compound 13 | 4H | 3 | Grade 0 | 105 | Δ |
| Comparative Example | Compound a | 2H | 3 | Grade 1 | 75 | X |
| | Compound b | 4H | 5 | Grade 1 | 84 | ○ |

As can be seen from Table 3, compared to compound a, the advantages in terms of hardness, flexibility, adherence, and heat resistance were highly significant after the disclosed polyfunctional oxetane-based compounds were used in a cationic photocuring system; while compared to compound b having a more similar structure, these compounds also exhibited better properties in terms of flexibility, adherence, and heat resistance and had more excellent overall properties.

In summary, the polyfunctional oxetane-based compound of the disclosed compound have excellent application properties in a cationic photocuring system, good adjustability of structures and properties, and can satisfy various application requirements.

Those described above are merely preferred Examples and are not intended to be limiting. With respect to the person skilled in the art, there may be various modifications and variations of this invention. All of modifications, equivalent replacements, improvements, and the like, which are within the spirit and the principle of this invention, should be encompassed in the scope protected by this invention.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A cation polymerizable monomer generated by a reaction of a polyfunctional oxetane-based compound and epichlorohydrin, wherein the polyfunctional oxetane-based compound has a structure represented by formula (I):

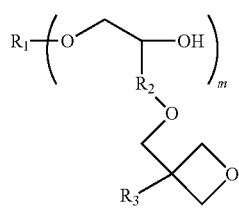

(I)

wherein, $R_1$ represents a $C_1$-$C_{40}$ linear m-valent alkyl group, a $C_1$-$C_{40}$ branched m-valent alkyl group, a $C_2$-$C_{20}$ m-valent alkenyl group, or a $C_6$-$C_{40}$ m-valent aryl group, wherein —$CH_2$— can be substituted with an oxygen atom, —NH—, or

provided that two —O-'s are not directly connected, and wherein one or more hydrogen atoms in these groups can be each independently substituted with an alkyl group, a halogen, or a nitro group, $R_2$ represents a $C_1$-$C_{20}$ linear alkylene group or a $C_1$-$C_{20}$ branched alkylene group, wherein —$CH_2$— in the main chain can be substituted with an oxygen atom, provided that two —O-'s are not directly connected, and wherein one or more hydrogen atoms in the group can be each independently substituted with an alkyl group, a halogen, or a nitro group, $R_3$ represents hydrogen, a halogen, a nitro group, a $C_1$-$C_{20}$ linear alkyl group, a $C_1$-$C_{20}$ branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_2$-$C_{10}$ alkenyl group, or a $C_6$-$C_{20}$ aryl group, wherein one or more hydrogen atoms in these groups can be each independently substituted with an alkyl group, a halogen, and a nitro group, and m represents an integer selected from 1-8; and wherein the cation polymerizable monomer has a structure represented by formula (IV):

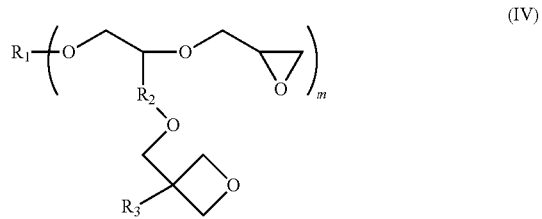

(IV)

wherein $R_1$, $R_2$, $R_3$, and m have the same definitions as those for formula (I).

2. The cation polymerizable monomer according to claim 1, wherein m is selected to be a numeric value of 2 or more; or when m=1, $R_1$ is substituted by at least one oxetanyl group.

3. The cation polymerizable monomer according to claim 1, wherein $R_1$ represents a $C_1$-$C_{40}$ linear m-valent alkyl group, a $C_1$-$C_{40}$ branched m-valent alkyl group, a $C_2$-$C_{10}$ linear m-valent alkenyl group, a $C_2$-$C_{10}$ branched m-valent alkenyl group, or a $C_6$-$C_{30}$ m-valent aryl group, wherein —$CH_2$— can be substituted with an oxygen atom, —NH—, or

provided that two —O-'s are not directly connected, and wherein one or more hydrogen atoms in these groups can be each independently substituted with an alkyl group, a halogen, or a nitro group.

4. The cation polymerizable monomer according to claim 1, wherein $R_2$ represents a $C_1$-$C_{10}$ linear alkylene group or a $C_1$-$C_{10}$ branched alkylene group, wherein —$CH_2$— in the main chain can be substituted with an oxygen atom, provided that two —O-'s are not directly connected.

5. The cation polymerizable monomer according to claim 1, wherein $R_3$ represents hydrogen, a $C_1$-$C_{10}$ linear alkyl group, a $C_1$-$C_{10}$ branched alkyl group, a $C_3$-$C_{10}$ cycloalkyl group, a $C_4$-$C_{10}$ cycloalkylalkyl group, a $C_4$-$C_{10}$ alkylcycloalkyl group, a $C_2$-$C_8$ alkenyl group, or a phenyl group.

6. The cation polymerizable monomer according to claim 1, wherein m is an integer selected from 1-6.

7. The cation polymerizable monomer according to claim 1, wherein m is an integer selected from 1-4.

8. The cation polymerizable monomer according to claim 1, wherein $R_1$ is: a $C_1$-$C_{12}$ linear 1-to-4-valent alkyl group, a $C_1$-$C_{12}$ branched 1-to-4-valent alkyl group, a $C_2$-$C_6$ linear 1-to-4-valent alkenyl group, a $C_2$-$C_6$ branched 1-to-4-valent alkenyl group,

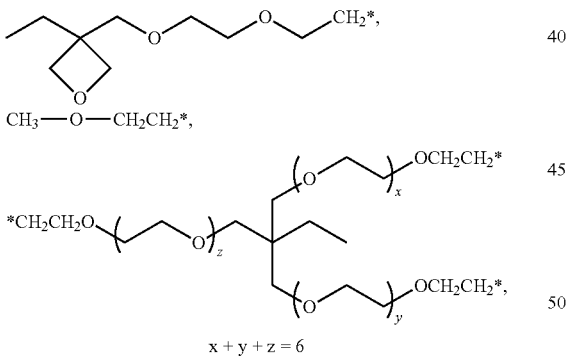

x + y + z = 6

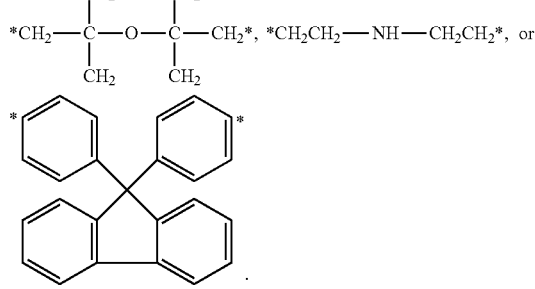

wherein * represents a bond, wherein x is an integer selected from the range of 0 to 6, y is an integer selected from the range of 0 to 6, and z is an integer selected from the range of 0 to 6.

9. The cation polymerizable monomer according to claim 1, wherein $R_3$ represents a $C_1$-$C_4$ linear alkyl group, a $C_1$-$C_4$ branched alkyl group or a $C_4$-$C_8$ cycloalkylalkyl group.

10. A production method of the cation polymerizable monomer represented by formula (IV) of claim 1, wherein the production method comprises performing a reaction, under a basic condition at one or more reaction temperatures selected from 25-120° C., between a polyfunctional oxetane-based compound represented by formula (I) and epichlorohydrin to obtain the cation polymerizable monomer, wherein a reaction formula is as follows:

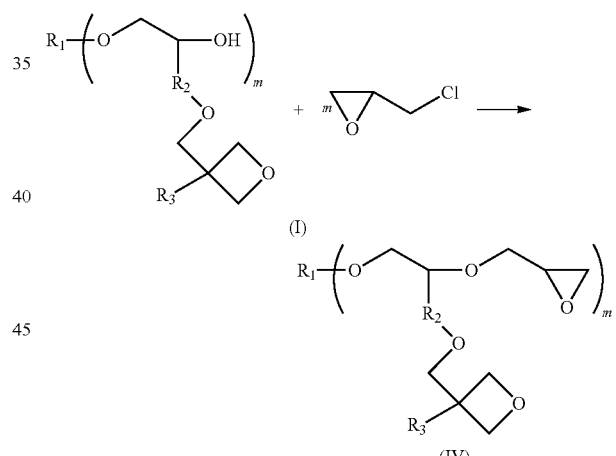

* * * * *